(12) United States Patent
Hebeisen et al.

(10) Patent No.: US 12,144,903 B2
(45) Date of Patent: Nov. 19, 2024

(54) SANITIZING WINDOW SHADE SYSTEM

(71) Applicant: Mechoshade Systems, LLC, Middleton, WI (US)

(72) Inventors: Stephen P. Hebeisen, Amawalk, NY (US); Eugene Miroshnichenko, Oceanside, NY (US)

(73) Assignee: MECHOSHADE SYSTEMS, LLC, Middleton, WI (US)

( * ) Notice: Subject to any disclaimer, the term of this patent is extended or adjusted under 35 U.S.C. 154(b) by 392 days.

(21) Appl. No.: 17/241,574

(22) Filed: Apr. 27, 2021

(65) Prior Publication Data

US 2021/0330837 A1    Oct. 28, 2021

Related U.S. Application Data

(60) Provisional application No. 63/016,117, filed on Apr. 27, 2020.

(51) Int. Cl.
*E06B 9/42* (2006.01)
*A61L 2/10* (2006.01)
(Continued)

(52) U.S. Cl.
CPC .............. *A61L 2/10* (2013.01); *A61L 2/18* (2013.01); *E06B 9/42* (2013.01); *E06B 9/68* (2013.01);
(Continued)

(58) Field of Classification Search
CPC .......... A61L 2/10; A61L 2/18; A61L 2202/14; E06B 9/42; E06B 9/68; E06B 2009/6809;
(Continued)

(56) References Cited

U.S. PATENT DOCUMENTS 3,007,036 A    10/1961  Mills, Jr.
3,271,568 A *   9/1966  Lundberg ............ F21V 33/0016
                                                       362/151
(Continued)

FOREIGN PATENT DOCUMENTS

AT         399200       3/1995
AU       2016222320     9/2016
(Continued)

OTHER PUBLICATIONS

Combined Search and Examination Report dated Mar. 9, 2017 in GB Application No. GB1618179.4.
(Continued)

*Primary Examiner* — Johnnie A. Shablack
*Assistant Examiner* — Matthew R. Shepherd
(74) *Attorney, Agent, or Firm* — SNELL & WILMER L.L.P.

(57) ABSTRACT

A window shade pocket system comprises a pocket; a roller shade mounted within the pocket; and an ultraviolet (UV) light source within the pocket. The system may also include a controller that controls a motor engaged to the roller shade, wherein the controller controls the speed of the motor to allow a portion of the roller shade to be under the UV light source for a predetermined amount of time to allow for sanitization of the portion of the roller shade. The method may comprise adjusting, by a processor, a roller shade within a pocket; and activating, by the processor, an ultraviolet (UV) light source within the pocket, wherein the UV light source sanitizes at least a portion of the roller shade.

18 Claims, 13 Drawing Sheets

(51) Int. Cl.
  *A61L 2/18* (2006.01)
  *E06B 9/68* (2006.01)
(52) U.S. Cl.
  CPC ... *A61L 2202/14* (2013.01); *E06B 2009/6809* (2013.01)
(58) Field of Classification Search
  CPC ....... E06B 2009/6818; E06B 2009/247; E06B 9/08; E06B 9/13; E06B 9/17007
  See application file for complete search history.

(56) References Cited

U.S. PATENT DOCUMENTS

| | | | |
|---|---|---|---|
| 4,060,310 A | 11/1977 | Brown | |
| 4,156,270 A | 5/1979 | Beatty | |
| 4,169,658 A | 10/1979 | Brown | |
| 4,254,813 A | 3/1981 | Vecchiarelli | |
| 4,404,770 A | 9/1983 | Markus | |
| 4,753,025 A | 6/1988 | Wennstrom | |
| 5,046,380 A | 9/1991 | Matsumoto | |
| 5,067,540 A | 11/1991 | Besler | |
| 5,121,782 A * | 6/1992 | Renkhoff | E04F 10/0618 |
| | | | 160/22 |
| 5,148,849 A | 9/1992 | Faludy | |
| 5,296,964 A | 3/1994 | Shopp | |
| 5,413,161 A | 5/1995 | Corazzini | |
| 6,111,694 A | 8/2000 | Shopp | |
| 6,230,782 B1 | 5/2001 | Reichert | |
| 6,253,492 B1 | 7/2001 | Finke | |
| 6,388,404 B1 | 5/2002 | Schnebly | |
| 6,410,908 B1 | 6/2002 | Anderson et al. | |
| 6,421,175 B1 | 7/2002 | Shopp | |
| 6,446,394 B1 | 9/2002 | Finke | |
| 6,532,109 B1 | 3/2003 | Shopp | |
| 6,645,392 B2 | 11/2003 | Frankenbach et al. | |
| 6,736,186 B2 | 5/2004 | Anderson | |
| 6,816,308 B1 | 11/2004 | Shopp | |
| 6,873,461 B1 | 3/2005 | McPherson, Jr. | |
| 7,559,707 B2 | 7/2009 | Shopp | |
| 7,714,335 B2 | 5/2010 | Beckers et al. | |
| 7,754,625 B2 | 7/2010 | Hendriks et al. | |
| 8,277,827 B2 | 10/2012 | Toreki et al. | |
| 8,349,447 B2 | 1/2013 | Nakayama et al. | |
| 8,407,914 B2 | 4/2013 | Hollinger et al. | |
| 8,505,865 B2 | 8/2013 | Wills | |
| 8,684,062 B2 | 4/2014 | Ng | |
| 8,816,301 B2 | 8/2014 | Stibich et al. | |
| 8,932,535 B2 | 1/2015 | Hyde et al. | |
| 9,115,537 B2 | 8/2015 | Blair | |
| 9,121,837 B2 | 9/2015 | Chan et al. | |
| 9,210,784 B2 | 12/2015 | Antoniazzi | |
| 9,517,284 B1 | 12/2016 | Stibich et al. | |
| 9,617,785 B2 | 4/2017 | Chou | |
| D808,684 S | 1/2018 | Santilli | |
| 9,872,495 B2 | 1/2018 | Kirshenbaum et al. | |
| 10,322,197 B1 * | 6/2019 | Williams | A61L 9/20 |
| D854,855 S | 7/2019 | Garcia Garcia | |
| 10,456,496 B2 * | 10/2019 | Munn | A61L 2/26 |
| 10,493,176 B2 | 12/2019 | McCormick et al. | |
| 10,544,619 B2 | 1/2020 | Hall et al. | |
| 10,561,750 B2 | 2/2020 | Mintie et al. | |
| 2004/0144506 A1 * | 7/2004 | Walter | B60J 1/208 |
| | | | 160/370.22 |
| 2004/0166018 A1 | 8/2004 | Clark et al. | |
| 2005/0118239 A1 | 6/2005 | Sabesan | |
| 2005/0205216 A1 | 9/2005 | Vrielink | |
| 2006/0188582 A1 | 8/2006 | Naylor Da Rocha Gomes | |
| 2007/0184276 A1 | 8/2007 | Thiemann et al. | |
| 2008/0045103 A1 | 2/2008 | Flippin et al. | |
| 2008/0193761 A1 | 8/2008 | Gomes et al. | |
| 2008/0230187 A1 | 9/2008 | Caron | |
| 2008/0289775 A1 | 11/2008 | Lukas | |
| 2009/0025321 A1 | 1/2009 | Cherney et al. | |
| 2010/0059186 A1 * | 3/2010 | Colson | E06B 9/262 |
| | | | 160/133 |
| 2011/0250409 A1 | 10/2011 | Marte et al. | |
| 2011/0256234 A1 | 10/2011 | Marte et al. | |
| 2011/0283620 A1 * | 11/2011 | Drifka | E05F 15/60 |
| | | | 49/70 |
| 2011/0308917 A1 * | 12/2011 | Lathem | A61L 2/10 |
| | | | 250/492.1 |
| 2013/0068398 A1 | 3/2013 | Wills | |
| 2013/0079732 A1 | 3/2013 | Burt et al. | |
| 2013/0079733 A1 | 3/2013 | Burt et al. | |
| 2013/0240661 A1 * | 9/2013 | Wills | E06B 9/42 |
| | | | 242/615 |
| 2014/0050612 A1 * | 2/2014 | Kneissl | A61L 2/10 |
| | | | 250/435 |
| 2015/0034843 A1 * | 2/2015 | Antoniazzi | H05G 2/00 |
| | | | 160/127 |
| 2015/0218177 A1 | 8/2015 | Chattopadhyay et al. | |
| 2017/0053068 A1 | 2/2017 | Pillai et al. | |
| 2017/0114593 A1 * | 4/2017 | Hebeisen | E06B 9/17007 |
| 2017/0362827 A1 | 12/2017 | Geiger | |
| 2018/0014681 A1 | 1/2018 | Stibich et al. | |
| 2018/0044847 A1 | 2/2018 | Swamy et al. | |
| 2018/0106102 A1 | 4/2018 | Holt et al. | |
| 2018/0163465 A1 * | 6/2018 | Biedermann | E06B 9/72 |
| 2018/0202157 A1 * | 7/2018 | Neal | E04B 9/30 |
| 2018/0230740 A1 | 8/2018 | Hall et al. | |
| 2019/0209722 A1 | 7/2019 | Stibich et al. | |
| 2019/0309173 A1 | 10/2019 | Lu | |
| 2019/0351084 A1 | 11/2019 | Garner et al. | |
| 2020/0063447 A1 | 2/2020 | Brinkman | |
| 2020/0131846 A1 * | 4/2020 | Hebeisen | G09F 15/0062 |
| 2020/0297619 A1 | 9/2020 | Ambrogio et al. | |

FOREIGN PATENT DOCUMENTS

| | | | | |
|---|---|---|---|---|
| AU | 2017200995 | | 8/2018 | |
| CN | 100521943 | | 8/2009 | |
| CN | 201578618 U | * | 9/2010 | |
| CN | 201764615 | | 3/2011 | |
| CN | 102439210 | | 12/2015 | |
| CN | 106192370 | | 6/2018 | |
| CN | 108584838 A | * | 9/2018 | ............... B67B 3/20 |
| CN | 209137432 | | 7/2019 | |
| CN | 106822943 | | 11/2019 | |
| CN | 110644914 | | 1/2020 | |
| DE | 3806611 | | 9/1989 | |
| DE | 102007059388 | | 6/2009 | |
| DE | 102011116707 | | 4/2013 | |
| DE | 202012103629 | | 11/2013 | |
| EP | 1534888 | | 6/2005 | |
| EP | 2602421 | | 6/2013 | |
| EP | 2631415 | | 8/2013 | |
| EP | 2843178 | | 8/2013 | |
| EP | 3521543 | | 8/2019 | |
| ES | 2452878 | | 4/2014 | |
| FR | 2845725 | | 4/2004 | |
| FR | 2911364 | | 7/2008 | |
| GB | 2542330 | | 3/2017 | |
| JP | 2000192757 | | 7/2000 | |
| JP | 2003221987 | | 8/2003 | |
| JP | 2004033648 A | * | 2/2004 | |
| JP | 2004076300 | | 3/2004 | |
| JP | 2005177149 | | 7/2005 | |
| JP | 2014214524 | | 1/2010 | |
| JP | 2013108238 | | 6/2013 | |
| JP | 2013170441 | | 9/2013 | |
| JP | 2014234593 | | 12/2014 | |
| KR | 20110031810 | | 3/2011 | |
| KR | 102136900 | | 9/2014 | |
| KR | 101789653 | | 10/2017 | |
| WO | 2006003348 | | 1/2006 | |
| WO | 2008017176 | | 2/2008 | |
| WO | 2008101363 | | 8/2008 | |
| WO | 2009059457 | | 5/2009 | |
| WO | 2010115183 | | 10/2010 | |
| WO | 2011061480 | | 5/2011 | |
| WO | WO-2016072945 A1 * | | 5/2016 | ............... C02F 3/082 |

(56) References Cited

FOREIGN PATENT DOCUMENTS

WO         2019086322         5/2019
WO         2020066130         4/2020

OTHER PUBLICATIONS

Examination Report dated Jul. 6, 2017 in GB Application No. GB1618179.4.
Notice of Allowance dated Jan. 4, 2018 in Canadian Application No. 2,946,634.
Office Action dated Aug. 30, 2017 in Canadian Application No. 2,946,634.
USPTO, Restriction/Election Requirement dated Aug. 6, 2018 in U.S. Appl. No. 15/334,591.
USPTO, Non-Final Office Action dated Sep. 17, 2018 in U.S. Appl. No. 15/334,591.
USPTO, Final Office Action dated Apr. 24, 2019 in U.S. Appl. No. 15/334,591.
USPTO, Advisory Action dated May 16, 2019 in U.S. Appl. No. 15/334,591.
USPTO, Non-Final Office Action dated Jun. 13, 2019 in U.S. Appl. No. 15/334,591.
USPTO, Notice of Allowance dated Sep. 20, 2019 in U.S. Appl. No. 15/334,591.
USPTO, Non-Final Office Action dated May 28, 2020 in U.S. Appl. No. 16/728,339.
USPTO, Notice of Allowance dated Jul. 24, 2020 in U.S. Appl. No. 16/728,339.

\* cited by examiner

SANITIZING WINDOW SHADE SYSTEM

CROSS-REFERENCE TO RELATED APPLICATIONS

This disclosure claims priority to, and the benefit of, U.S. provisional patent application No. 63/016,117, filed on Apr. 27, 2020 and entitled "Sanitizing Window Shade System," which is hereby incorporated by reference in its entirety for all purposes.

FIELD

This disclosure relates to window shade systems, and more particularly, to a pocket or cassette that includes one or more systems for sanitizing a window shade.

BACKGROUND

Window shade systems typically include a pocket (or space) for mounting the shade and another pocket for housing the wiring associated with the shade and other electronics. The window shade installer must often determine where to locate each of the pockets. The locations of the pockets may be important for not only accessibility, but also to comply with certain fire codes. An important part of the decision for the pocket location is the different codes that may apply to different areas. For example, items that exist in a room may be subject to different fire codes than items that exist in the ceiling or plenum. Such codes may determine if the contractor needs to include plenum cable or non-plenum cable. The type of jacket surrounding the cable may be impacted by the location of the cable.

The plenum spaces are between a drop and standard ceiling. The plenum spaces may also similarly exist in the floor space. These spaces are where the air in a building circulates, so these spaces are used to aid in heating and cooling functions. While non-plenum (PVC) cable is less expensive, plenum cable is often required when no conduit is used in the plenum spaces. Fire and smoke travel quickly in plenum spaces. As such, the levels of toxicity in the smoke from a fire are typically lower since plenum cable includes a jacket that is often comprised of flame-resistant material (e.g., Teflon). The flame-resistant material results in the cable smoking less than regular non-plenum (PVC) cable and the smoke that is emitted is less toxic. If the window shade pocket can be considered to be part of the room (and not part of the plenum), then the less expensive non-plenum cabling can be used in the pocket.

Moreover, a pocket that holds a window shade may be a very long structure. Because different pockets may need to accommodate different size shades, the pockets may vary in size. Furthermore, the pockets may include different features which may need to be incorporated into the pocket walls. The design of a pocket should take into consideration all of these features, while still being designed to be as lightweight and inexpensive as possible.

SUMMARY

In various embodiments, the disclosure includes a window shade pocket system comprising a pocket: a roller shade mounted within the pocket; and an ultraviolet (UV) light source within the pocket. The UV light source may at least partially sanitize at least one of the roller shade, the pocket or components within the pocket. The system may also include a controller that controls a motor engaged to the roller shade, wherein the controller controls the speed of the motor to allow a portion of the roller shade to be under the UV light source for a predetermined amount of time to allow for sanitization of the portion of the roller shade. The portion of the roller shade may be the portion that was exposed to the room. The speed may be based on at least one of an amount or extent of bacteria or viruses on at least one of the roller shade or in a room.

In various embodiments, the system may also comprise a central UV light source, wherein the roller shade provides a barrier from UV light from the central UV light source. The system may include vertical channels, wherein the UV light source is within the vertical channels. The system may include a controller that adjusts an intensity of UV light from the UV light source. The controller may also allow the UV light source to be activated during certain time periods. The UV light source may be at least one of between the window shade and the window; or between the room and the window shade. The UV light source may include a plurality of UV light sources. The UV light source may include a plurality of UV light sources that are coupled together and rotate together. The UV light source may include LED strip lighting. The UV light source may include a lens.

In various embodiments, the system may include a first bracket removably affixed to an inside surface of a first wall of the pocket, wherein the first bracket retains the UV light source. The UV light source may be at least one of removeable from a first bracket in the pocket or rotatable within the first bracket. The first bracket may retain non-plenum cabling, wherein the non-plenum cabling extends within the pocket. The system may comprise a subsystem for dispersing sanitizing solution.

In various embodiments, the method may comprise adjusting, by a processor, a roller shade within a pocket; and activating, by the processor, an ultraviolet (UV) light source within the pocket, wherein the UV light source sanitizes at least a portion of the roller shade. The method may further comprise controlling, by the processor, a speed of the adjusting such that a portion of the roller shade is under the UV light source for a predetermined amount of time to allow for sanitization of the portion of the roller shade.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the detailed description and claims when considered in connection with the drawing figures.

DETAILED DESCRIPTION

As set forth in more detail in the attached drawings, the present disclosure includes cabling and other components 110 (e.g., power plug, splitter, electrical components, etc.) in the window shade pocket (or cassette) 100. The window shade pocket 100 may be outside of the plenum and considered part of the room, and not part of the ceiling. However, the window shade pocket 100 may be in the plenum, but the pocket 100 may still be considered part of the room. By including the cabling and other components in the window shade pocket 100, the cabling may not need to meet the more restrictive and more expensive ceiling fire codes. As such, the less expensive non-plenum (e.g., PVC) cabling may be used in the pocket 100.

This application includes the subject matter of U.S. patent application Ser. No. 16/728,339 filed on Dec. 27, 2019 and entitled "Wired Pocket With Lighting." The '339 application is a continuation-in-part of, and claims priority to and the benefit of, U.S. patent application Ser. No. 15/334,591 filed on Oct. 26, 2016 and entitled "Wired Pocket." The '591 application claims priority to, and the benefit of, U.S. Provisional Application Ser. No. 62/247,036 filed on Oct. 27, 2015 and entitled "Wired Pocket." All of the above-identified applications are hereby incorporated by reference in their entirety for all purposes.

In various embodiments, the cabling and other components 110 may be incorporated into the window shade pocket 100 in any manner. In this manner, the pocket 100 combines the functionality of a mounting space (e.g., for roller shades) and wiring space. In various embodiments, the window shade pocket 100 may include one or more permanent or removable channel that retains the cables and/or other components 110. In various embodiments, the pocket 100 and/or brackets 105 may be comprised of aluminum or non-metallic material. In various embodiments, the pocket 100 and/or brackets 105 may also be modular to support various ceiling systems and attachments. In various embodiments, the brackets 105 may be continuous down all or a portion of the pocket 100 (as set forth in FIG. 6) or may be spaced periodically along the inside of the pocket 100 (as set forth in FIG. 7).

Figure 6:
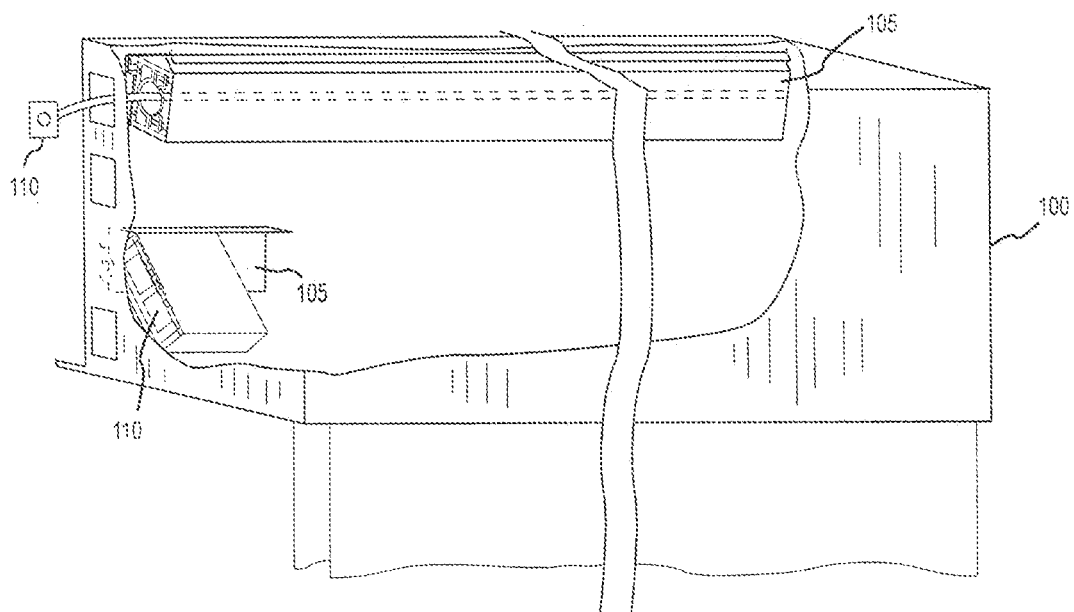
FIG. 6 is an exemplary diagram of a cut-away view of a window shade pocket showing a full first bracket, a second bracket and cabling, in accordance with various embodiments.
Figure 7:
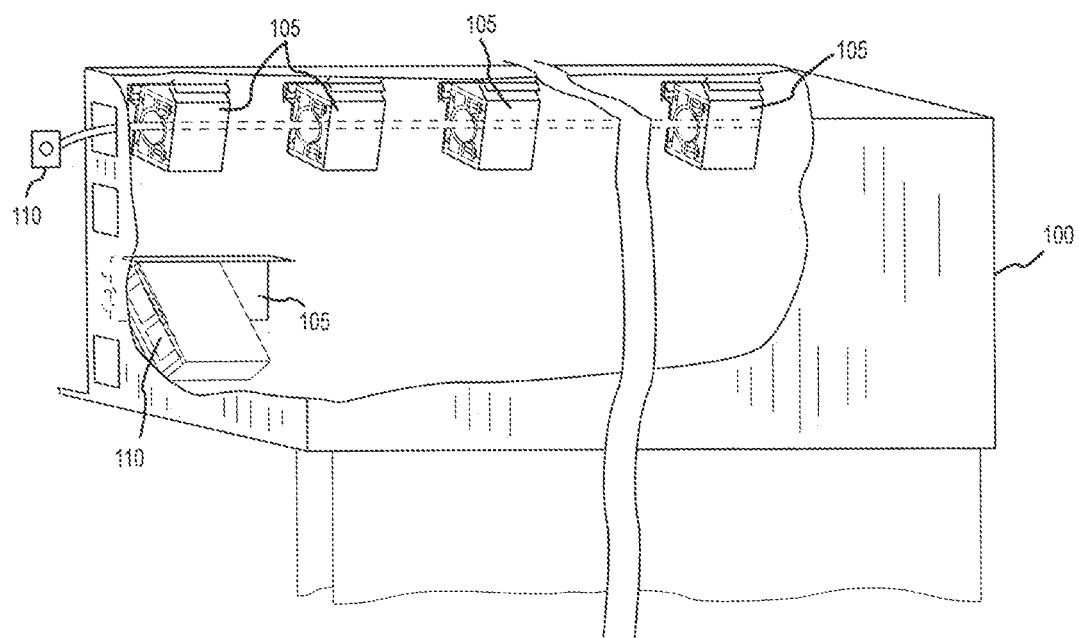
FIG. 7 is an exemplary diagram of a cut-away view of a window shade pocket showing a plurality of first brackets, a second bracket and cabling, in accordance with various embodiments.

In various embodiments, and as set forth in FIGS. 6-7, the cables may be held in the channels directly. Hooks, retaining clips and/or springs may allow access to the cabling. Clip-in-brackets 105 may be included to reduce weight and to reduce the cost of pocket 100. The clip-in-brackets 105 may be the entire length of the pocket 100, over a portion of the pocket 100 and/or multiple brackets 105 over specified separation mounting distances. The brackets 105 may mount on one or more of the faces of the pocket 100. The shade 115 may be removed (or more easily removed) after the retaining clip or channel is removed. The shade may also be removed around the bracket, while the bracket 105 is still installed.

The brackets 105 may be mounted to allow the roller shade to operate without impacting the bracket. The cabling may be serviced while protecting the cables from physical access or exposure to the rotating shade 115. In various embodiments, additional safety features may be incorporated into the system such as, for example, methods of separation of high and low voltage cabling to meet code (e.g., distance versus metal barrier). In various embodiments, the pocket 100 may be grounded and/or a junction box may be included in the pocket 100. In various embodiments, the pocket 100 may include venting options such as, for example, pre-punched holes and/or a removable back wall where a punched sheet can be inserted. Such venting features can even be added after installation. The hole sizes may be variable. The pocket 100 and brackets 105 may include features to prevent or minimize vibration for various attachments.

Figure 8:
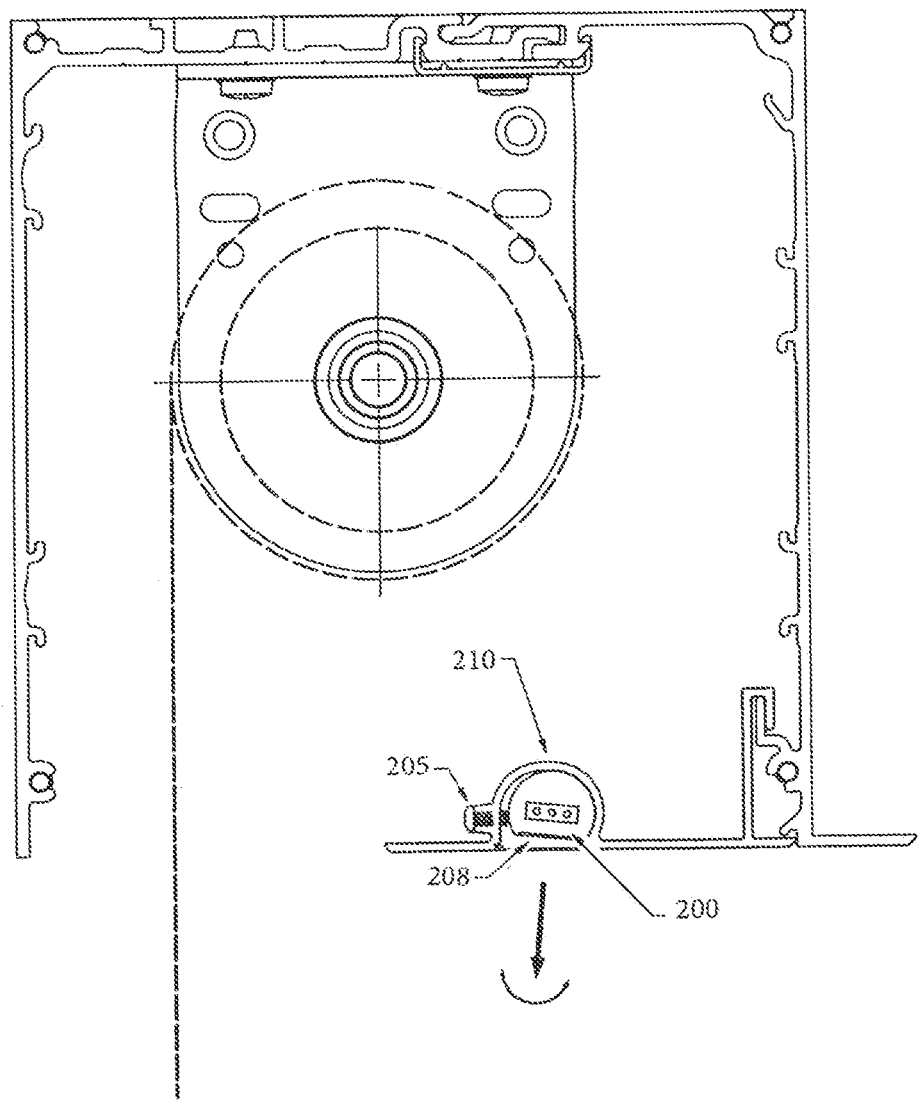
FIG. 8 is an exemplary diagram of a cut-away view of a window shade pocket showing a light source inserted into a bottom bracket attached to the pocket, in accordance with various embodiments.
Figure 9:
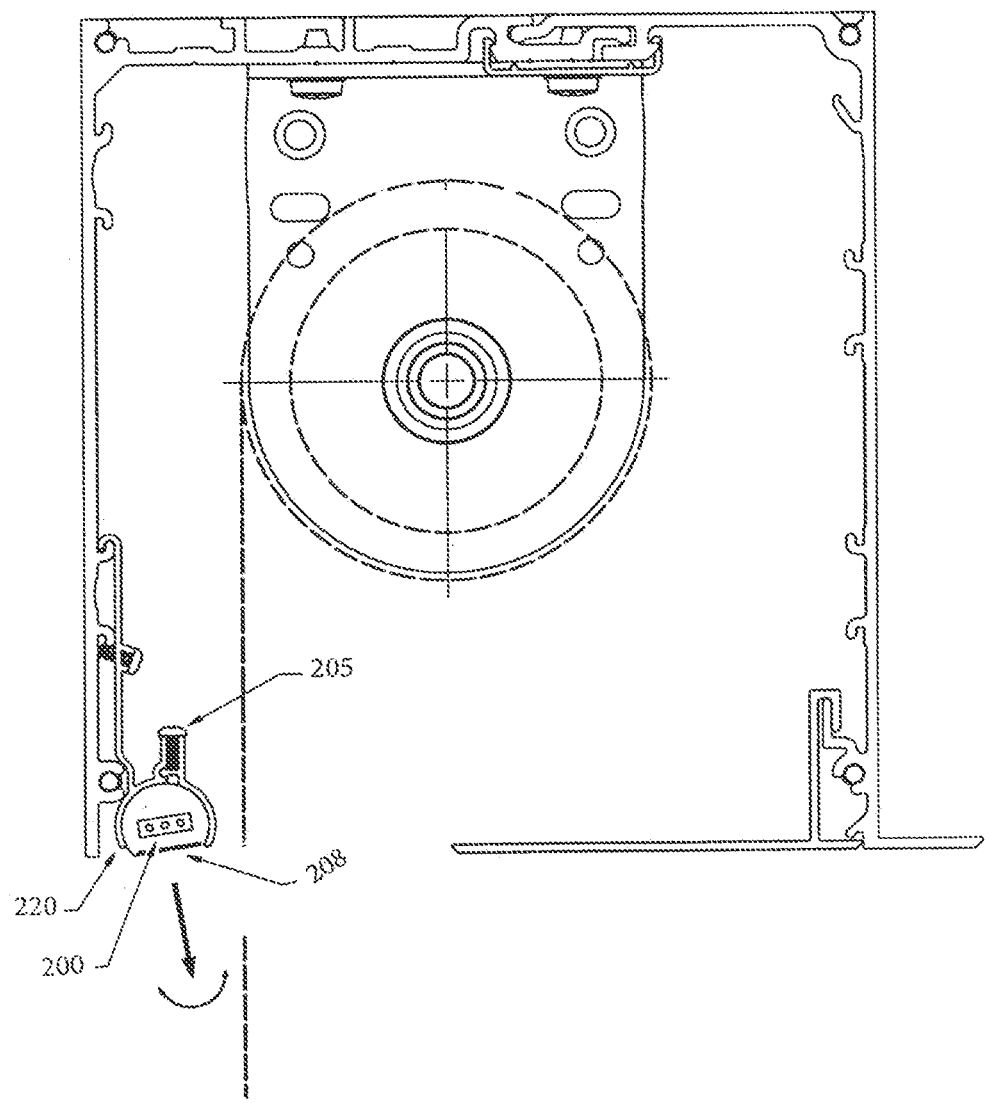
FIG. 9 is an exemplary diagram of a cut-away view of a window shade pocket showing a light source inserted into a side bracket attached to the pocket, in accordance with various embodiments.

More specifically, and in various embodiments, the window shade pocket 100 system may comprise a pocket 100 having an inside surface, a bracket 105 removably affixed to the inside surface of the pocket 100 and a roller shade 115 within the pocket 100. The inside surface of the pocket 100 may include a first wall 120, a second wall 125 and a third wall 130, wherein the third wall 130 includes the bracket 105 retaining the cabling. The bracket 105 may retain cabling and/or electrical components 110 within the bracket. The electrical components 110 may include a light source 200 and associated wiring, as shown in FIGS. 8-12. Light source 200 may provide visible light and/or UVC light. Bracket 105 may include a bracket 210 or 220, as shown in FIGS. 8 and 9, that is configured to retain light source 200. The bracket 105 may include a plurality of brackets 105 along the inside surface of the pocket 100, wherein the cabling is retained within the plurality of brackets 105. The bracket 105 may form a channel between the bracket 105 and the inside surface of the pocket 100. The roller shade 115 may be able to be removed after the bracket 105 is removed or the roller shade 115 may be able to be removed while the bracket 105 is still affixed to the inside surface of the pocket 100.

Figure 1:
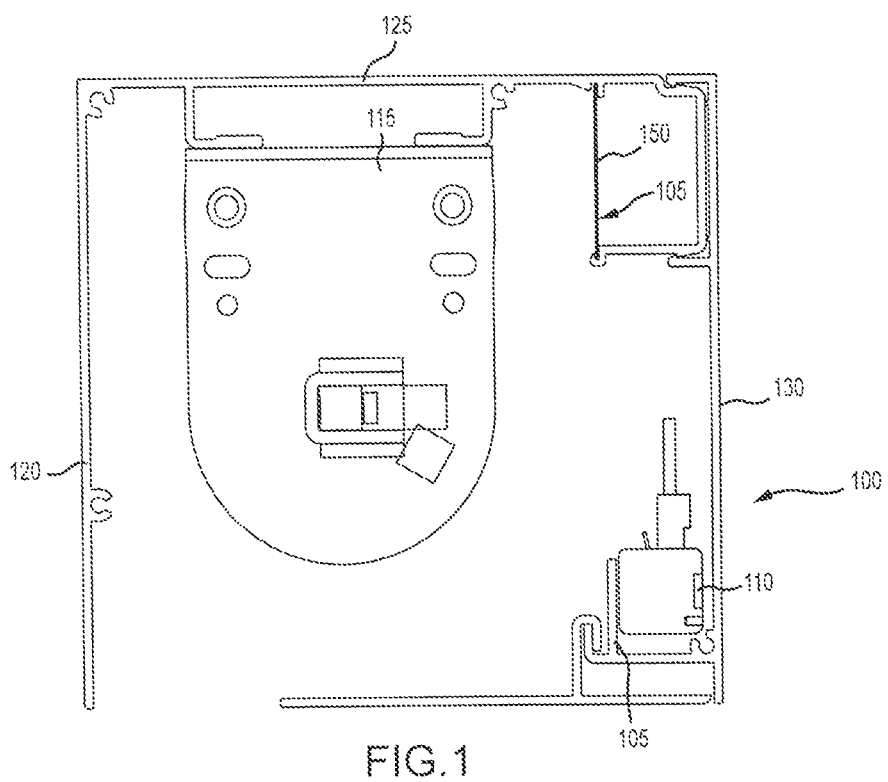
FIG. 1 is a schematic diagram of a window shade pocket with a roller shade and a planar bracket, in accordance with various embodiments.
Figure 2:
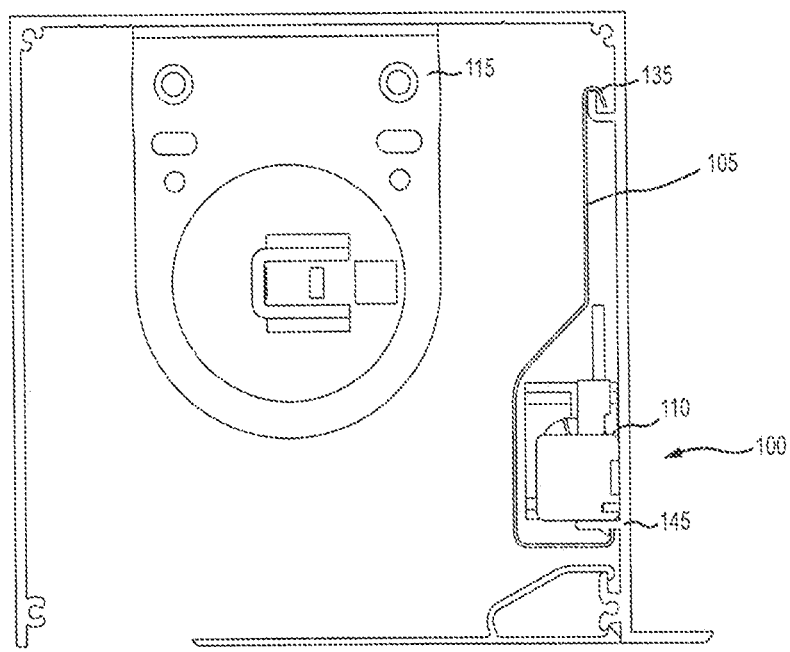
FIG. 2 is a schematic diagram of a window shade pocket with a roller shade and a bracket having a bent metal retaining clip, in accordance with various embodiments.
Figure 3:
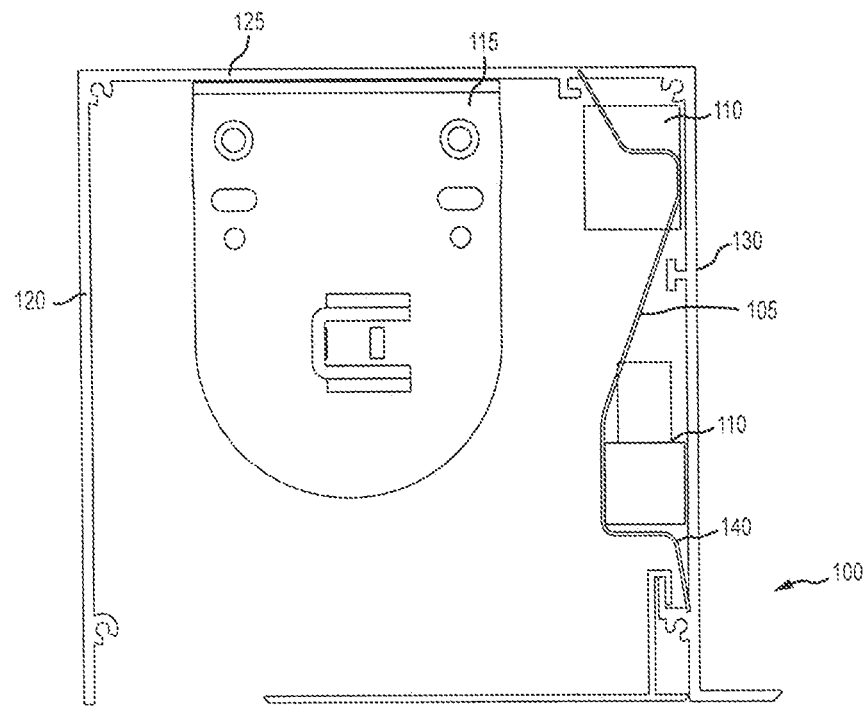
FIG. 3 is a schematic diagram of a window shade pocket with a roller shade and a bracket having a spring clip, in accordance with various embodiments.

In various embodiments, the bracket 105 may include a bent metal retaining clip 135 (as shown in FIG. 2) and/or a spring clip 140 (as shown in FIG. 3). The end of the bracket 105 may be retained behind a lip 145 (as shown in FIG. 2)

extruding from a ledge. The end of the bracket 105 may be bent into an arc 135, wherein the arc is retained behind a lip extruding from a ledge. The bracket 105 may include a planar metal plate 150 (as shown in FIG. 1) having a top edge and a bottom edge, wherein the top edge is retained in a first channel and the bottom edge is retained in a second channel.

Figure 5:
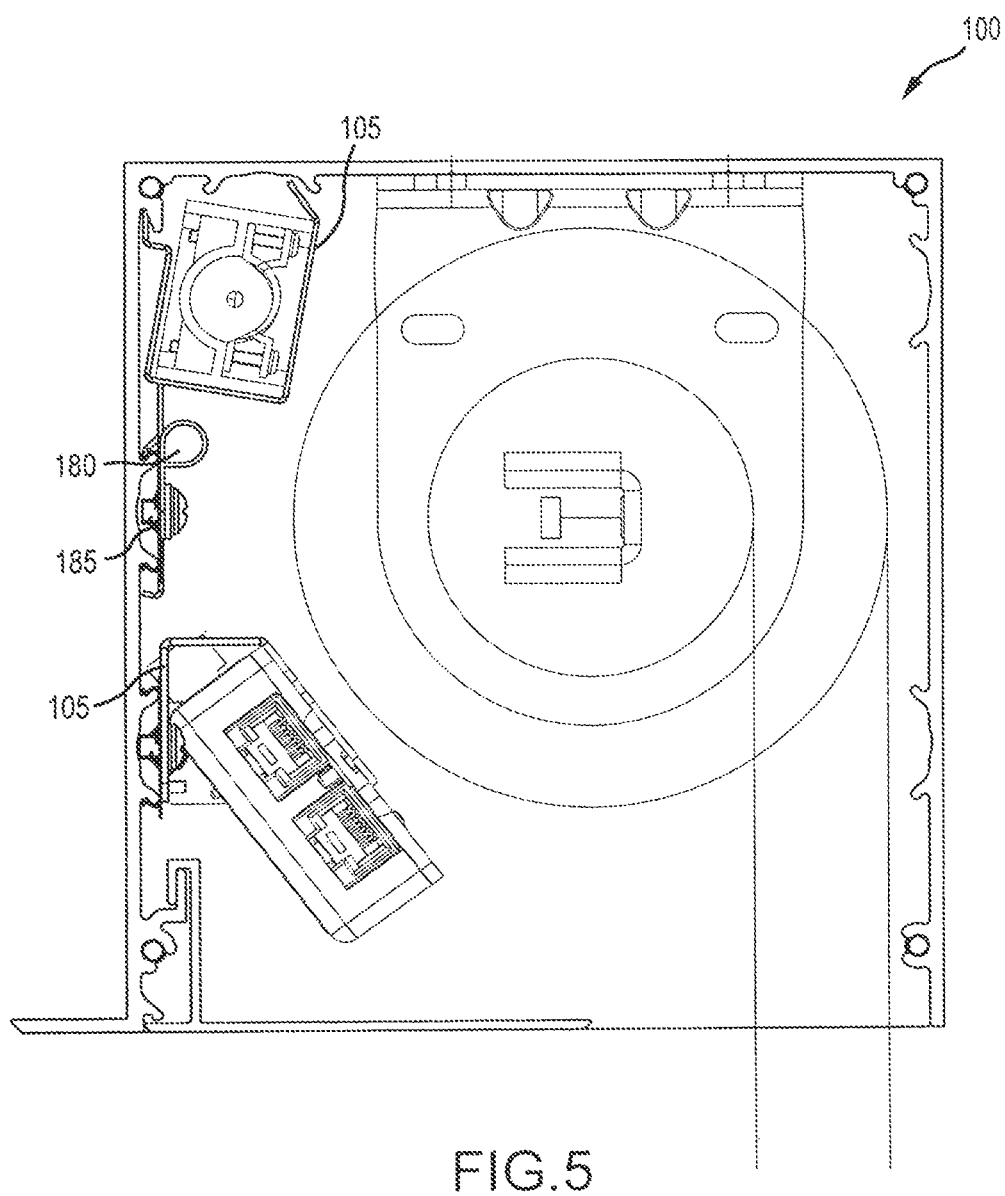
FIG. 5 is a schematic diagram of a window shade pocket with a roller shade and a additional bracket embodiments along with a cable clip, in accordance with various embodiments.

Additional bracket 105 embodiments are shown in FIG. 5 supporting different electronic components, but still avoiding contact with the roller shade. A cable clip 180 is also shown in FIG. 5. Cable clip 180 is configured to receive a cable and provide support for the cable, while keeping the cable close to the side wall of pocket 100. Cable clip 180 and/or bracket 105 may attach to the side wall of pocket 100 using, for example, miter angles 185. Miter angles 185 include curved ends that partially wrap around the lips protruding from the side wall. Upon tightening the fastener against the side wall, the curved ends tightly engage the lips protruding from the side wall, thereby securely fastening bracket 105 to the side wall of pocket 100.

Figure 4:
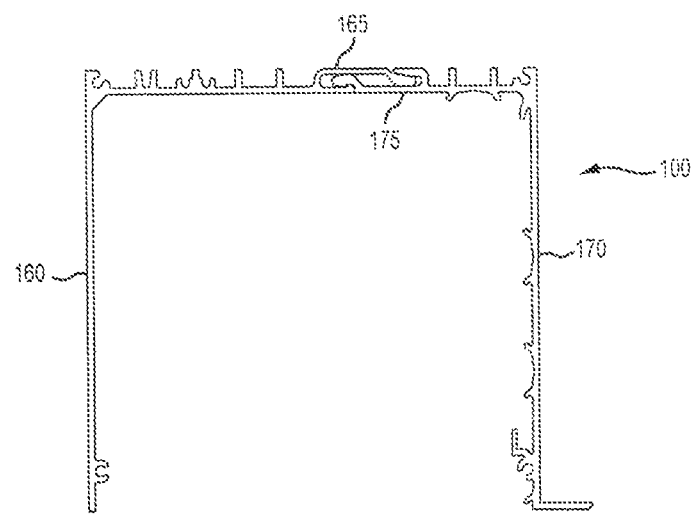
FIG. 4 is a schematic diagram of a window shade pocket showing the engagement device on the top wall, in accordance with various embodiments.

In various embodiments, and as shown in FIG. 4, the pocket 100 may be comprised of a first component 160 having a first engagement device 165 and a second component 170 having a second engagement device 175, wherein the first engagement device 165 engages the second engagement device 17 to form the pocket 100. Having the pocket 100 comprised of two components may allow for a smaller die to extrude the aluminum for each component. Moreover, having the pocket 100 comprised of two components provides the ability to have different widths assembled by only changing one of the components (extrusions). Having the pocket 100 comprised of two engaged components also provides the ability to have different features in the assembled pocket 100 by simply changing one of the extrusions. Furthermore, having the pocket 100 comprised of two engaged components also allows a design of the pocket 100 with thinner walls and thus makes the pocket 100 lighter and less expensive. However, having the pocket 100 comprised of two engaged components may not impact the brackets 105 and the electrical channels discussed herein because the engagement is on the top panel and not on the side panels where the brackets 105 may be inserted.

The disassembled pocket 100 may also be comprised of a first component 160 nested into a second component 170 to reduce space for shipping. The pocket 100 may be comprised of a first component and a replaceable second component, wherein the second component may be replaced with a third component (e.g., of a different size) that results in a different width of the pocket 100. Moreover, the second component 170 having a second bracket 105 may be replaced with a third component having a third bracket 105.

As briefly discussed above, bracket 105 may retain cabling and/or electrical components 110 within bracket 105. In various embodiments, the electrical components 110 may include a light source 200, as shown in FIGS. 8-11. The pocket may also include wiring or other components that support or are part of the light source. Bracket 105 may include a bracket 210, 220 or 230, as shown in FIGS. 8, 9 and 11 respectively, that is configured to retain light source 200. The light source may include, for example, any type of light bulb, light bar, light strip (e.g. LED lighting), reflective device (e.g., mirror), UVC light source and/or the like. An example of a light strip includes TSV16.4 Feet 300 Led RGB Muliticolor Changing RGB Led TV Backlight Strip Light Kit Sold By Wow Parts or the Monster Illumination Sound-Light Led 65" RGB Multicolor Changing Mood And Music Mode Light Strip sold by Monster. In various embodiments, the LED strips may be modular and extendable.

The lighting strips may connect via 2 or more pinholes on the end of the lighting strip for power. The lighting strips may also employ cable connectors. In various embodiments, the lighting strips may connect together with more connections when intelligent to accommodate both power and a network. For example, channel access may exist from the pocket area to the lighting strip. Such a configuration helps to ensure that the connection from the pocket wiring to the first lighting strip can be completed without having to machine the channel (or with minimal machining). The network could be POE (power over ethernet) which may power and network the light strip over a single cable or multi-pin connector. The network may also include wireless radio frequency to minimize cabling. Power may also be battery powered inside the pocket or inside the light strip. Via a network connection, the light source may be controlled and automated relative to on/off, dim level, frequency and/or color. Automation may be accomplished based on schedule, sunrise/sunset, ambient light level outside the building, ambient light level inside the building, occupancy, shade position, sky condition and/or circadian rhythm optimization for the occupant(s). When coupled together, the connected modular light sections may rotate together. When the light source is intelligent, the coupled sections may all illuminate the same, or if networked, the coupled sections may illuminate based on zone requirements.

In various embodiments, the bracket may be configured as an attachment to the pocket or to an enclosure, wherein the attachment is configured to receive the light source. The attachment 210, 220 or 230 may include an enclosure for the light source, such that the light source may be removed from the enclosure (e.g., to replace the bulb) and/or rotate within the enclosure (e.g., to point the light closer to the window shade). The system may include an interlock for a screw 205 (or a device with similar functionality) to affix the angular rotation of the light source. In various embodiments, this interlock may be positioned on the exterior surface of the pocket with the adjustment surface facing down in order to promote easy access to adjust the angle. Access to the adjustment may be hidden behind a decorative cover to help minimize view of such less aesthetic features from the room.

Figure 10:
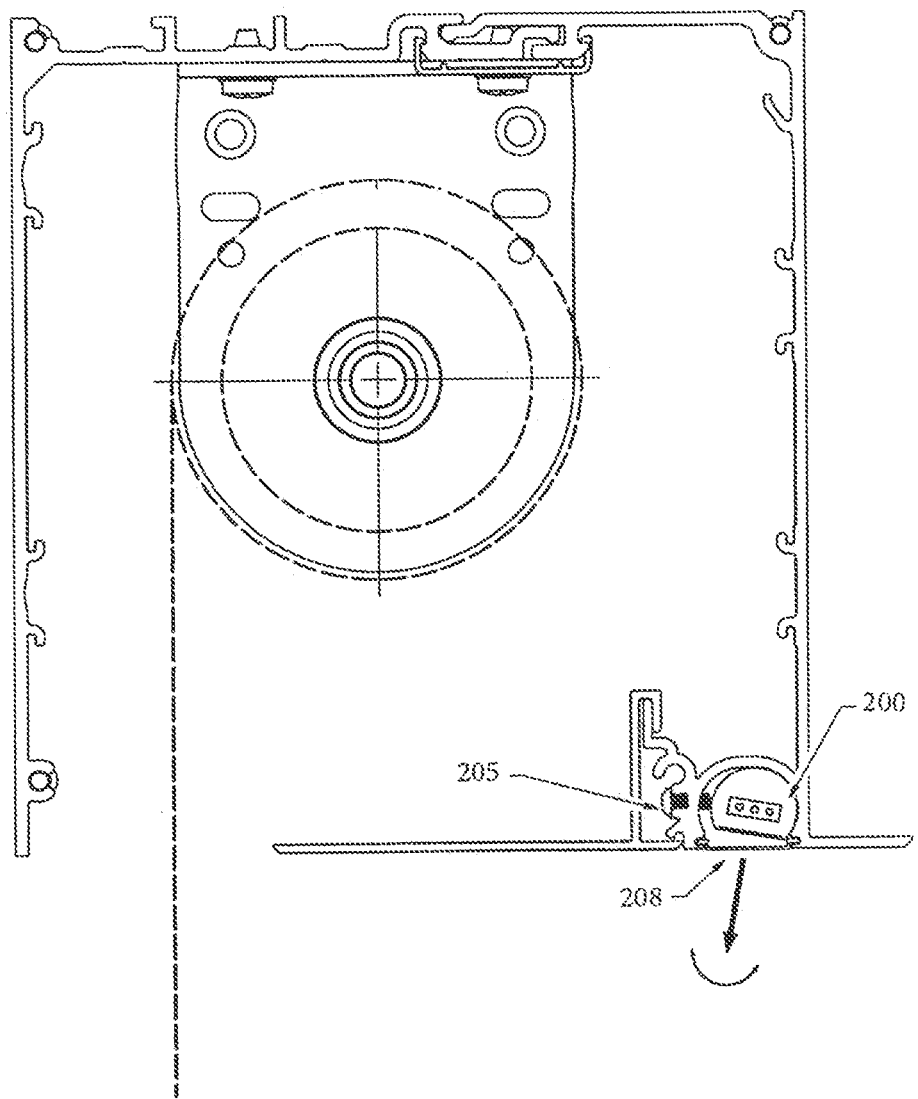
FIG. 10 is an exemplary diagram of a cut-away view of a window shade pocket showing a light source inserted into the bottom of the pocket, in accordance with various embodiments.
Figure 11:
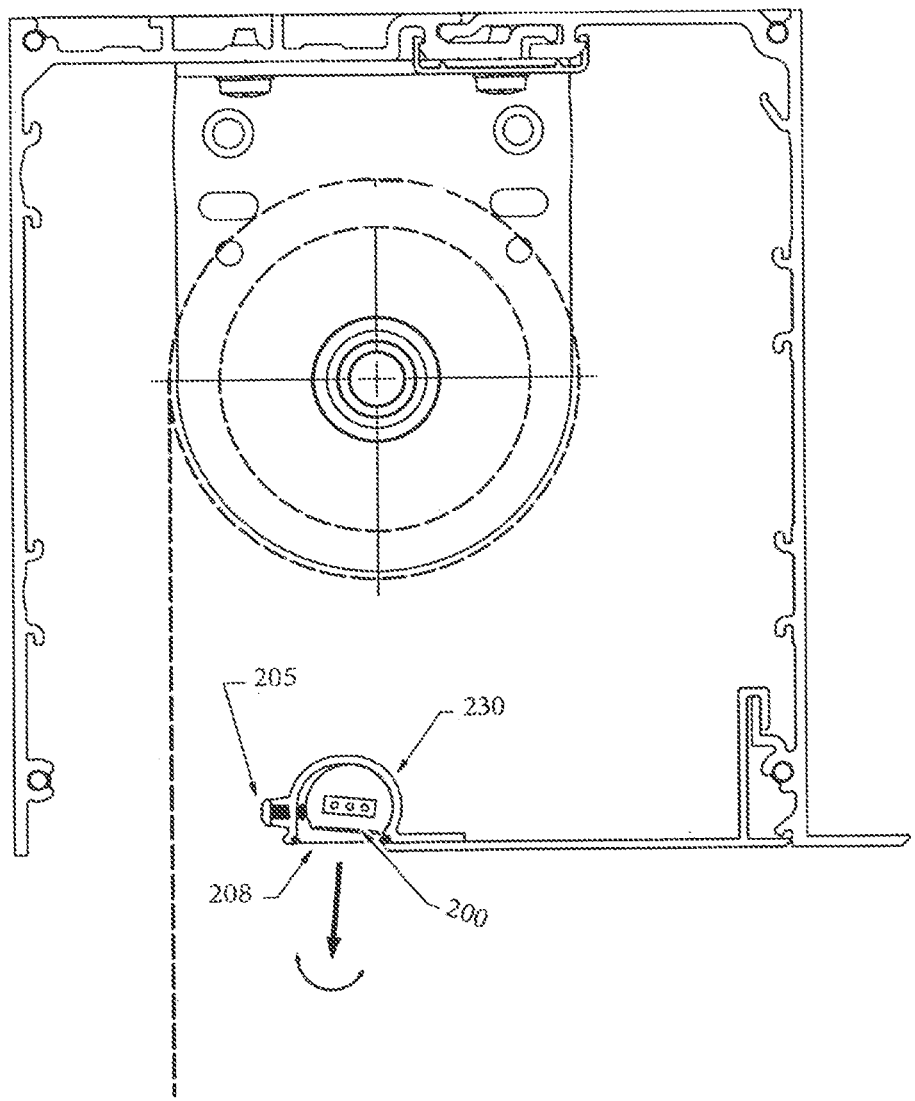
FIG. 11 is an exemplary diagram of a cut-away view of a window shade pocket showing a light source inserted into a bottom bracket attached to the end of an enclosure, wherein the enclosure is attached to the pocket, in accordance with various embodiments.

As set forth in FIG. 10, the light source may fit into a portion of the pocket (e.g., bottom portion). Because the pocket is stationary, the system includes a flexible mount to pop the light strip straight up and into the channel in the pocket from below. The light strip may also be slid into the channel. In various embodiments, when the LED strip section is installed into the pocket, and the wiring may not be in the removable closure portion (covering a portion of the open bottom of the pocket) because the closure portion may not need to include any wiring. Moreover, the closure portion may be removed or installed without impacting the light source.

As set forth in FIG. 8, the attachment may attach to the pocket (e.g., attach to the side of the pocket), but extend horizontally outward and allow the light source 200 to shine downward, with different embodiments shown in each figure. As set forth in FIG. 11, the attachment may attach to the enclosure, wherein the enclosure attaches to the pocket. These configurations may allow lighting the shade from the interior of the room. As set forth in FIG. 9), the attachment may attach to a side surface of the pocket. This configuration may light the shade from the window direction. The attachment may include one or more interlocking fingers to temporarily secure the attachment to the pocket wall. A light strip or light bar may slide into a groove in the bracket or in the pocket wall. Different attachment configurations and/or locations may allow the light source to be closer or farther from the fabric surface.

In various embodiments, the light source may be in front of and/or behind the window shade fabric. The light source may light the shade in order to promote a certain decorative cosmetic, or the lighting of the shade may serve functional purpose within the room. Window shade fabric may have a certain openness factor or it may be a solid, blackout material. The openness factor may allow someone from the outside of a building to partially or fully see through the fabric and into the building, particularly when a room is lit up inside the building at night. Privacy and restricted viewing through the shade may be achieved by having a light source brighten the shade from the side of the viewer.

When lighting the shade from the interior and/or exterior, the light source may also include different colors to adjust the color of the window shade. Such color change may impact (e.g., benefit) the tone of the room, or the circadian rhythm of its occupants. The color changes may be dependent upon the time of day, season of the year, current sky conditions, holidays, temperature, working conditions, activities around the window shades (e.g., party, work-out, work), etc.

In various embodiments, the system may minimize or avoid shadows on the window shade fabric. For example, the system may be configured to include the light bar farther away from the fabric to minimize light shadows on the fabric. If the fabric has wrinkles or does not hang down with a smooth surface, the light may cause unsightly shadows on the fabric. The use of the light source on the fabric surface may reduce or eliminate such unsightly shadows on the window shade fabric. The light source may also reduce or eliminate hot spots on the window shade fabric.

In various embodiments, the system may include a lens (or lens cover) 208 over the light source. Any type, color or configuration of lens 208 may be included in the system. The lens 208 may focus or broaden a beam from the light source to change the light beam's impact on the window shade fabric's surface. The lens 208 may be over the light source and snap into the attachment device or in the pocket wall. The lens 208 may be configured to focus the light from the light source over the window shade fabric. The lens 208 may focus the light over a certain portion of the fabric, evenly over the entire fabric, evenly over the portion of the fabric that covers a certain area (e.g. the portion that covers the window), away from the fabric or any other distribution of light. The lens 208 may include textures and/or films to help diffuse the light. The lens 208 may be tinted in order to help control the color of the light. Some light sources (e.g. LEDs) may be tunable in color and/or spectrum, so tinted lenses may not be required.

The lens (or lens cover) 208 may be configured in various ways. The lens 208 may be built into the housing of the lighting strip. The lens 208 may be attached to the lighting strip. The lens 208 may rotate independent of the LED which helps minimize wiring from affecting the ease of rotation. The lens 208 may also be changed onsite to optimize to field conditions (allows more flexibility on site).

Figure 12:
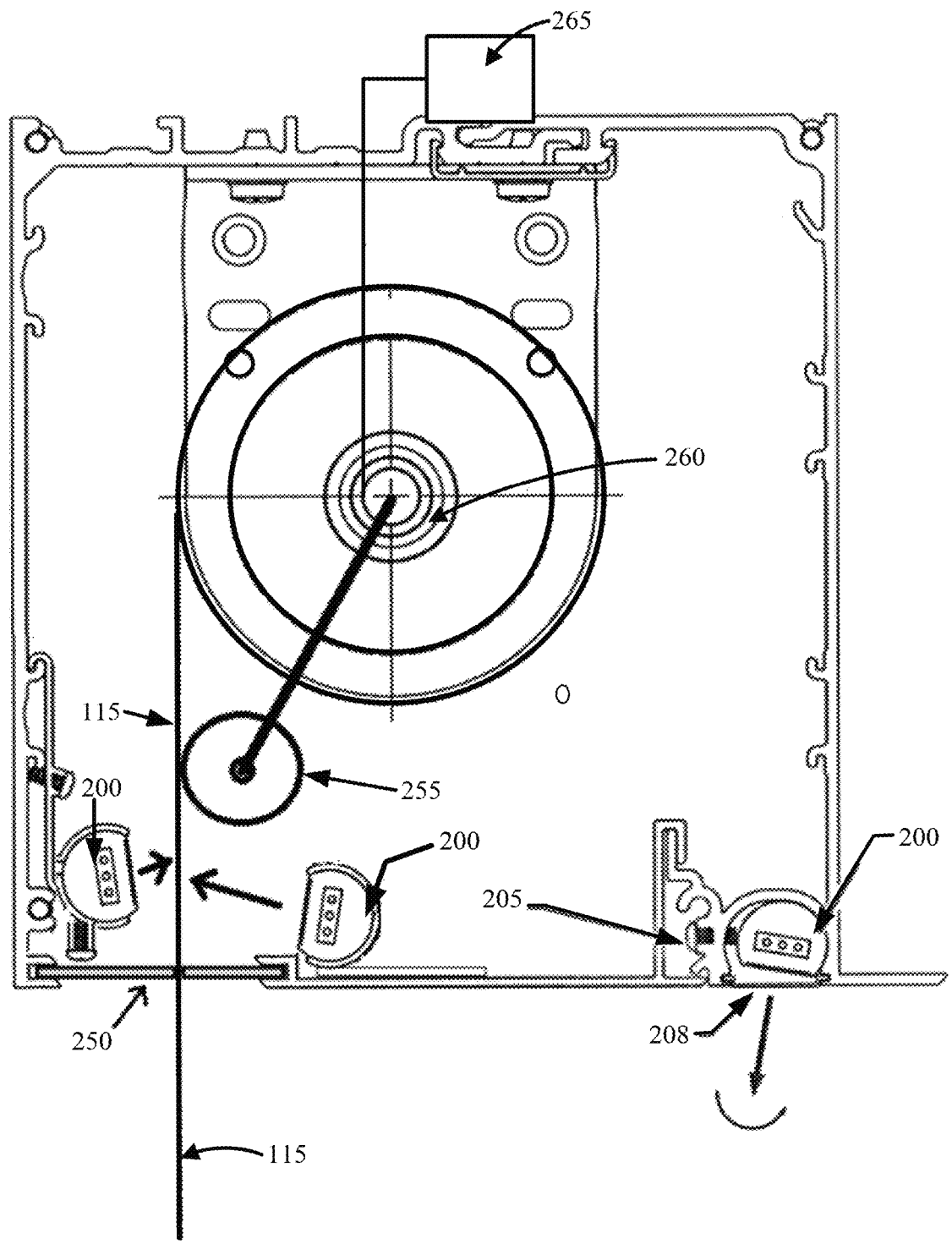
FIG. 12 is an exemplary diagram of a cut-away view of a window shade pocket showing UV light lights on both sides of the window shade fabric, a sponge roller to apply sanitizing solution to the window shade fabric, doors to restrict the UV light from exiting the pocket, and an optional visible light, in accordance with various embodiments.
Figure 13:
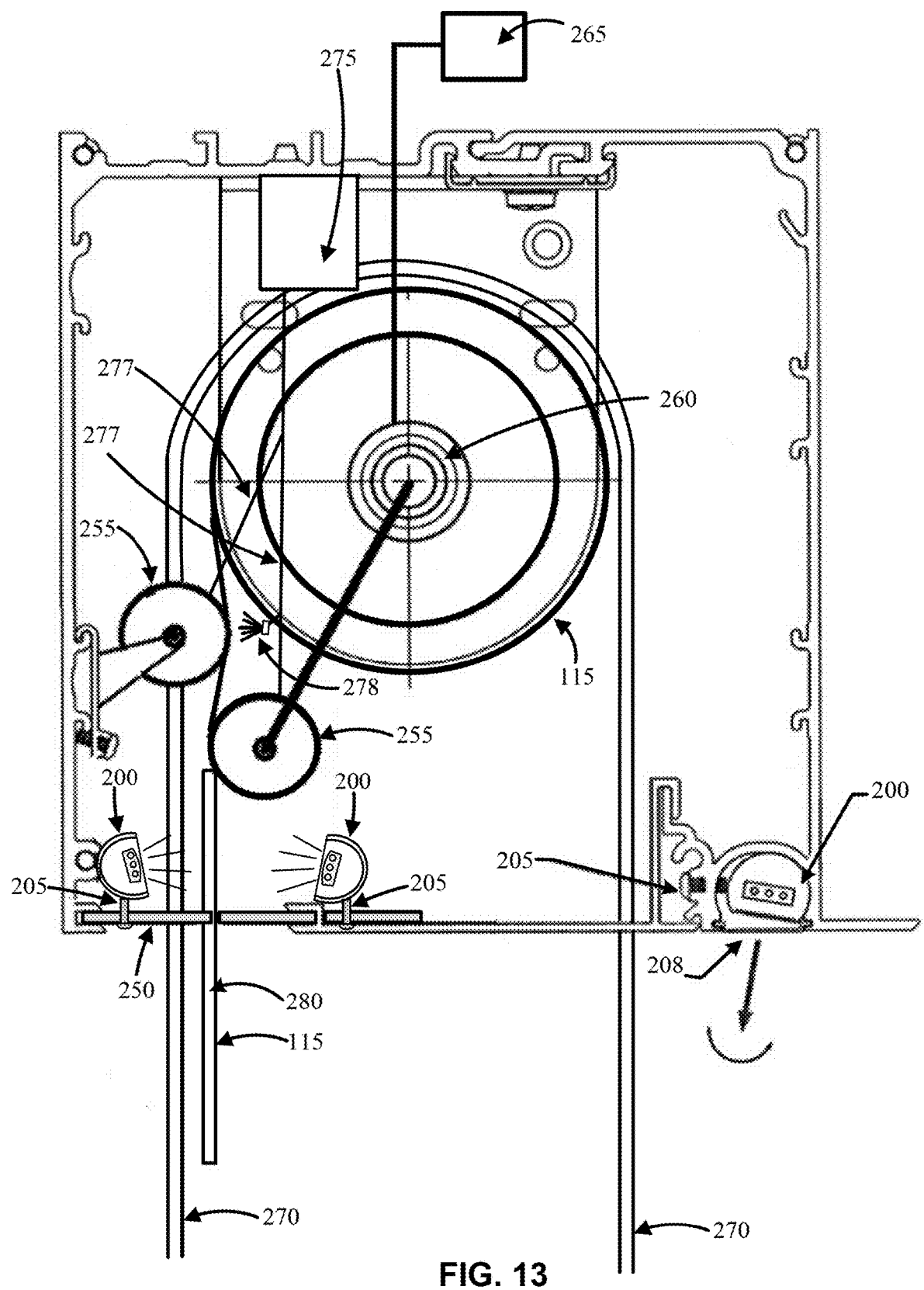
FIG. 13 is an exemplary diagram of a cut-away view of a window shade pocket showing sponge rollers on both sides of the window shade fabric, and an optional visible light, in accordance with various embodiments.

In various embodiments, and as shown in FIGS. 12-13, pocket 100 may include elements to fully or partially sterilize the window shade fabric 115, the bracket 200, the chain, the gears, the shaft, other components within pocket 100, the areas around pocket 100 and/or areas outside of pocket 100 (e.g., any portion or all of the room). While this disclosure may focus on sanitizing the window shade fabric 115, the features and functions may similarly apply to the bracket 200, the chain, the gears, the shaft, other components within pocket 100 or the areas around pocket 100. As discussed above, a pocket may be installed into a ceiling and along an entire length of a room. However, as used herein, pocket 100 may include any device that holds one or more window shade system components. For example, a pocket may be a cassette, a box, a cylinder or other retaining device. The cassette may include a roller shade, and be distributed as one unit, wherein the cassette may be installed over a window.

In various embodiments, the light source 200 may include a light source 200 that helps to partially or fully sterilize at least a portion of the window shade fabric 115 or other components. The pocket 100 may also include electronics 110, wiring or other components that support or are part of the light source 200. For example, light source 200 may include an ultraviolet (UV) light source 200 or any other source that may be configured to help sanitize a window shade, the pocket, components and/or surrounding areas. For example, light source 200 may include the UV germicidal lamps provided by LightTech LightSources. The ultraviolet light source 200 may disperse the UV light on at least a portion of the window shade, around the window shade, on one or more components of the bracket 200 and/or throughout at least a portion of the room.

The use of UV light may cause damage, drying out or brittleness to the textile materials or other components of the system, so the system may put limits on the amount of activation or intensity of the UV light source. Such limits to the activation or intensity of the UV light source may be based on an amount of time, number of days, season of the year, temperature, weather, communication with other systems (e.g., motion sensors, locks, lights, etc.) and/or other environmental conditions. For example, the system may only activate the UV sensors when no motion is detected in the area, when the lights are off and/or after business hours when the door locks to the room are activated. The system may activate the UV sensors during a maintenance schedule. The system may also include certain components that may be replaced as the components may degrade (e.g., spline).

In various embodiments, the UV light source 200 may include a lamp and/or strip technology. The strip technology may disperse the UV light over a wider area such that the UV light covers a larger portion of the window shade fabric 115. For example, the UV light source 200 with strip technology may extend across the entire width of the roll of window shade fabric 115. The strips may be modular and extendable. The UV light source and/or the strip technology may include light emitting diode (LED) technology. The UV light source 200 may be positioned in the pocket, but on one side of the window shade fabric 115 (e.g., to sanitize the inside of the fabric that is more exposed to the occupants of a building) or on both sides of the window shade fabric 115 (e.g., to sanitize both sides of the fabric). The UV light source may point toward the fabric, but also angled upward to minimize the UV light from exiting the pocket. The UV light source may also be located in a separate compartment or separate cassette that is permanently or removably mounted on pocket 100 or on another cassette. The pocket or cassette holding the roller shade may include an opening that mates with an opening in the separate compartment or separate cassette that contains the UV light, such that the UV light can enter the pocket or cassette from the separate compartment or separate cassette.

In various embodiments, pocket 100 may be further sealed or include extra components to further restrict the UV light from exiting the pocket 100 and restrict the UV light from impacting the room and its occupants. For example, the pocket 100 may include extra layers to cover gaps, reflectors to reflect the UV light back into the pocket and/or covers to further retain the UV light. As shown in FIG. 12, the opening in the pocket (where the window shade exits) may include one or more flaps or doors 250 that restrict the exit of the UV light. The flaps or doors may be flexible and/or rigid seals. The seals may prevent or reduce leakage of UV light for safety. Such flaps or doors 250 may be positioned to partially or fully cover the opening at all times. The flaps or doors 250 may be closed to partially or fully cover the opening, in response to the UV light being activated. The flaps or doors 250 may also open to allow the window shade to move, but be closed when the window shade stops moving. In that regard, the dispersion of the UV light may be limited to within the pocket as much as possible to avoid the UV light impacting people or other items in the room.

In various embodiments, the UV lighting strips may connect via two or more pinholes on the end of the UV lighting strip for power. The lighting strips may also employ cable connectors. In various embodiments, the UV lighting strips may connect together with more connections when the strip is an intelligent strip to accommodate both power and a network. For example, channel access may exist from the pocket 100 to the UV lighting strip. Such a configuration helps to ensure that the connection from the pocket 100 wiring to the first UV lighting strip can be completed without having to machine the channel (or with minimal machining). The network could be POE (power over ethernet) which may power and network the UV light strip over a single cable or multi-pin connector. The network may also include wireless radio frequency to minimize cabling. Power may also be battery powered inside the pocket 100 or inside the UV light strip. Via a network connection, the UV light source 200 may be controlled and automated relative to on/off, dim level, frequency, strobing, intermittently flashing and/or color. Automation may be accomplished based on schedule, sunrise/sunset, ambient light level outside the building, ambient light level inside the building, occupancy, shade position, sky condition and/or circadian rhythm optimization for the occupant(s). When coupled together, the connected modular UV light sections may rotate together. When the UV light source 200 is intelligent, the coupled sections may all illuminate the same, or if networked, the coupled sections may illuminate based on zone requirements.

In various embodiments, the bracket holding the UV light source 200 may be configured as an attachment to the pocket 100 or to an enclosure, wherein the attachment is configured to receive the UV light source 200. The attachment 210, 220 or 230 may include an enclosure for the UV light source 200, such that the light source 200 may be removed from the enclosure (e.g., to replace the UV bulb) and/or rotate within the enclosure (e.g., to point the UV light closer to the window shade). The system may include an interlock for a screw: 205 (or a device with similar functionality) to affix the angular rotation of the UV light source 200. In various embodiments, this interlock may be positioned on the exterior surface of the pocket 100 with the adjustment surface facing down in order to promote easy access to adjust the angle. A motor and a communication device may interface with the interlock, the light source 200 and/or the bracket holding the light source 200, thereby allowing remote operation of the interlock device and/or remote rotation of the light source 200. Access to the adjustment may be hidden behind a decorative cover to help minimize view of such less aesthetic features from the room.

As set forth in FIG. 10, in various embodiments, the UV light source 200 may fit into a portion of the pocket 100 (e.g., bottom portion). Because the pocket 100 is stationary, the system includes a flexible mount to pop the UV light strip straight up and into the channel in the pocket 100 from below. The UV light strip may also be slid into the channel. In various embodiments, when the UV LED strip section is installed into the pocket 100, and the wiring is not in the removable closure portion (covering a portion of the open bottom of the pocket 100) because the closure portion may not need to include any wiring. Moreover, the closure portion may be removed or installed without impacting the UV light source 200.

As set forth in FIG. 8, in various embodiments, the attachment may attach to the pocket 100 (e.g., attach to the side of the pocket 100), but extend horizontally outward and allow the UV light source 200 to shine downward, with different embodiments shown in each figure. As set forth in FIG. 11, the attachment may attach to the enclosure, wherein the enclosure attaches to the pocket 100. These configurations may allow lighting the window shade from the interior of the room. As set forth in FIG. 9, the attachment may attach to a side surface of the pocket 100. This configuration may light the window shade from the window direction. The attachment may include one or more interlocking fingers to temporarily secure the attachment to the pocket 100 wall. A UV light strip or UV light bar may slide into a groove in the bracket or in the pocket 100 wall. Different attachment configurations and/or locations may allow the UV light source 200 to be closer or farther from the fabric surface.

In various embodiments, the system may include a lens (or lens cover) 208 over the UV light source 200. Any type, color or configuration of lens 208 may be included in the system. The lens 208 may focus or broaden a beam from the UV light source 200 to change the UV light beam's impact on the window shade fabric 115 surface. The lens 208 may be over the UV light source 200 and snap into the attachment device or in the pocket 100 wall. The lens 208 may be configured to focus the UV light from the UV light source 200 over the window shade fabric 115. The lens 208 may focus the UV light over a certain portion of the fabric, evenly over the entire fabric, evenly over the portion of the fabric that covers a certain area (e.g. the portion that covers the window), away from the fabric or any other distribution of UV light. The lens 208 may include textures and/or films to help diffuse the UV light. The lens 208 may be tinted in order to help control the color of the UV light.

The lens (or lens cover) 208 may be configured in various ways. The lens 208 may be built into the housing of the UV lighting strip. The lens 208 may be attached to the UV lighting strip. The lens 208 may rotate independent of the UV light source 200 which helps minimize wiring from affecting the ease of rotation. The lens 208 may also be changed onsite to optimize to field conditions (allows more flexibility on site).

In various embodiments, the system may control the window shade fabric 115 to roll up and/or down at a speed such that the UV light source 200 may expose the window shade fabric 115 for a certain time period to sterilize the window shade fabric 115 as the window shade fabric 115 passes through the UV light source 200. A user may manually adjust the window shade fabric 115 (e.g., by pulling on a chain 270) at any chosen speed such that different portions of the window shade fabric 115 are under the UV light during the time the user adjusts the fabric. The user may operate a switch or a control system (e.g., controller 265) may provide input to activate a motor 260 that adjusts the window shade fabric 115. The system may control (e.g., using controller 265) the speed of the motor 260 to allow the window shade fabric 115 to be under the UV light (and/or adjust the intensity of the UV light) for a certain amount of time. The system may schedule certain times of days, days of the week, and/or seasons to operate the UV light. For example, the system may obtain data from the internet or other data feeds, then operate the UV light more often during higher incidences of sicknesses in certain regions, during flu season in the winter, during an epidemic and/or during high allergy days.

In various embodiments, the system may cause the portion of the fabric that was more exposed to the room to be under the UV light (and/or adjust the intensity of the UV light) for a longer period of time. In that regard, the system may determine starting points when the fabric is rolled up, and ending points where the window shade fabric 115 is fully or partially over the window (or at any other point). Moreover, different starting points or ending points may be established by the user or the system. For example, the user may override the window shade movement by stopping the window shade at a certain point over the window; or the system may set the window shade at certain points over the window such that the window shade fabric 115 partially or fully blocks the solar rays, but the window shade fabric 115 does not cover the lower portion of the window and allows daylight through the lower portion of the window. The system may then use those starting points and ending points (only partially down the window) to determine which portion of the fabric was more exposed in the room.

In various embodiments, the system may test the window shade fabric 115 (or obtain information about the window shade fabric 115) to determine the amount or extent of bacteria or viruses that exist on the window shade fabric 115. The system may also test the room or area where the window shade fabric 115 is located (or obtain information about the room or area) to determine the amount or extent of bacteria or viruses that exist in the room or area. The system may then use such data to determine the speed (e.g., using controller 265) at which the motor 260 should move the window shade fabric 115 under the UV light (and/or the intensity of the UV light) to sufficiently sanitize the window shade fabric 115 (e.g., remove a customized amount and/or certain percentage of the bacteria and viruses). For example, when a room is determined to include an increased amount of bacteria or viruses (e.g., increased over a yearly average amount), the system may increase (e.g., using controller 265) the intensity of the UV light and/or slow the movement of the window shade such that particular portions of the window shade are exposed to the UV light for a longer period of time.

In various embodiments, other subsystems, sources, chemicals or products may be included in or around the pocket 100 (e.g., in reservoir 275) to further partially or fully wash and/or sterilize the window shade fabric 115, the bracket 200, the chain 270, the gears, the shaft, other components within pocket 100, the areas around pocket 100, and/or the user interfaces (e.g., keypad, chain 270, hembar, etc.). Such a washing or sterilizing cycle may be repeated depending on the extent of sterilization desired or may be scheduled and/or implemented similar to the various steps and factors discussed above for the UV light implementation (e.g., seasons, occupancy, etc.). For example, pocket 100 may include a subsystem (e.g., in reservoir 275) for dispersing antimicrobial, antimildew, antiviral, germocide and/or any other sanitizing or disinfectant solution. The sanitizing solution may be formed from a powder or pellet additives. The sanitizing solution may be sprayed onto the fabric (e.g., via sprayer 278), sprayed into the fabric and/or baked into the fabric. For example, the system may include a heat lamp (or use the above UV lamp) configured for applying heat after the solution is sprayed onto the fabric. Moreover, a laminate containing the sanitizing solution may be applied over the window shade fabric. In various embodiments, the system may include a storage basin (e.g., in reservoir 275) for holding the sanitizer or the system may acquire the sanitizer from another tank or location (e.g., connect to a jug or piped in from another area). The system may also include piping 277, pumps, nozzles and sprayers lined partially or fully across the pocket 100. As shown in FIG. 12, a sponge 255 and/or spray nozzles may disperse the sanitizing solution on the window shade, around the window shade, the bracket 200, any components in the pocket and/or throughout at least a portion of the room. The sanitizing system may operate similar to a misting system such as, for example, Mist Works Gulf Breeze High-Pressure Residential Misting System Kit distributed by Mist Works (ID #2892842 Model #MKGB12-1), the details of which are hereby incorporated by reference for all purposes.

One or more of the pocket 100, cassette, the window shade fabric 115, the bracket 200, the chain, the gears, the shaft, other components within pocket 100, the areas around pocket 100, and/or the user interfaces (e.g., keypad, chain, hembar, etc) may include an additive or coating that comprises antimicrobial, antimildew; antiviral, germicide and/or any other sanitizing or disinfectant solution to reduce the spread of germs or other diseases. Such sanitizing material may be baked into the components. The sanitizing material may be light activated in that the sanitizing material may react with moisture to form a reactive oxygen species. For example, the keypad may include a coating or additive in the plastic and/or glass. The chain or hembar may include coatings or additives to the metal (e.g., polyurethane powder). The system may further minimize physical interaction by incorporating or integrating a voice or gesture control system to provide instructions for operating the functions of the window shade system.

In various embodiments, the pocket may include a sprayer that applies disinfectant over one or both sides of the window shade fabric. In various embodiments, the pocket may include a dispensing sponge 255 (e.g., in the form of a rectangle, roller or wand) that slides over one or both sides of at least a portion of the window shade fabric. The wand or sponge 255 may move along the fabric. The sponge 255 may maintain the fabric in a single plane. The sponge 255 may apply sanitizer to the fabric as the fabric is rolled up or down across the sponge 255. The system may provide periodic, continuous or replacement sanitizing solution to the wand or sponge 255. The sponge 255 may be allowed to be depleted of sanitizing solution. The sponge 255 may then be refilled with sanitizing solutions from reservoir 275 via piping 277. The sponge 255 may be configured to dip into a tub of the sanitizing solution to re-fill the sponge 255. The sponge 255 may be refilled by inserting sanitizing solution through the wall or door of the pocket and onto the sponge 255. The sponge 255 may be replaceable with a new wand or sponge 255 that includes more sanitizing solution. The sanitizing solution may include or contain similar ingredients as, for example, Purell® surface disinfectant and/or sanitizer spray supplied by GOJO Industries, Inc of Akron, Ohio. Such disinfectants may include Ethyl Alcohol, Isopropyl Alcohol, bleach and/or any other disinfectant components.

A window shade system may include a chain 270. The chain 270 may be comprised of stainless steel, nickel plating, plastic or any other material. The chain 270 may be pulled to cause rotation of the shaft to thereby raise or lower the window shade. Because the chain 270 is often touched by various people, a system for sanitizing the chain is also desired. The pocket 100 may include a reservoir or storage tank (e.g., in reservoir 275) with sanitizing solution, such that the chain 270 rotates through the reservoir 275 and the chain 270 is sanitized. The chain 270 may also rotate through the sprayers, wand or sponge 255, as described above. The UV light may also disperse over the chain 270 when the chain 270 rotates through the pocket, and/or while the chain 270 is hanging down below the pocket. The pulling of the chain 270 may activate the UV light, and/or the stopping of the pulling of the chain 270 may activate the UV light (indicates that the chain 270 was touched and needs to be cleaned).

In various embodiments, the system may include a covering 280 over one or more surfaces of at least a portion of the window shade fabric 115. The covering 280 may cover the portion of the window shade that is unrolled or may cover the entire window shade. Any portion of the covering 280 may include a layer of antimicrobial, antimildew, antiviral and/or any other sanitizing or disinfectant solution. Such solution may be incorporated into the covering 280 material. The covering 280 may be disposable. The covering 280 may be attached to the window shade surface. The covering 280 may be partially or fully attached by clips, staples and/or glue. The covering 280 may include similar glue as, for example, a Post-it® Note by 3M Corporation, such that the covering 280 may be applied to the window shade fabric 115 and easily removed while leaving minimal or no glue on the window shade fabric 115.

In various embodiments, the system may trigger a central UV light source or sprayer (e.g., anywhere within a room) to sanitize all (or a subset of) surfaces in an area. The area may include, for example, a screening area or a triage area. The area may be evacuated, prior to performing the UV light or spray sterilization. While the central UV light or spray is sanitizing, the window shade may also provide a safety barrier. For example, the window shade may protect against the UV light or spray exiting through the window, or a shade between rooms (or between areas) may restrict the UV light or spray from entering additional rooms or areas.

In various embodiments, the pocket 100 may also include vertical channels or the vertical channels may exist separate from pocket 100. The sides of the window shade fabric 115 may travel in, and be guided by, the vertical channels. The sides of the window shade fabric 115 may include attachments to help the window shade fabric 115 engage inside the channels. The vertical channels may support the sides of the window shade fabric 115 to reduce bending or disforming of the window shade fabric 115. However, the side portions of the window shade fabric 115 may not be exposed to the UV light or spray because the side portions of the window shade fabric 115 are concealed within the channels. Moreover, the attachments (e.g., zipper or other catch elements) within the channel would not be exposed to the UV light or spray. Therefore, the system may include a sprayer, sponge 255, UV light source 200 and/or UV strip lights within the channels.

The detailed description of exemplary embodiments herein makes reference to the accompanying drawings, which show exemplary embodiments by way of illustration and its best mode, and not of limitation. While these exemplary embodiments are described in sufficient detail to enable those skilled in the art to practice the invention, it should be understood that other embodiments may be realized and that logical, chemical and mechanical changes may be made without departing from the spirit and scope of the invention. For example, the steps recited in any of the method or process descriptions may be executed in any order and are not necessarily limited to the order presented. Moreover, many of the functions or steps may be outsourced to or performed by one or more third parties. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Systems and methods are provided. In the detailed description herein, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the invention. The scope of the invention is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Furthermore, no element, component, or method step in the present disclosure is intended to be dedicated to the public regardless of whether the element, component, or method step is explicitly recited in the claims. No claim element herein is to be construed under the provisions of 35 U.S.C. 112 (f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

The invention claimed is:

1. A window shade pocket system comprising:
   a pocket;
   a roller shade mounted within the pocket, wherein the roller shade is moved faster or slower, in response to a trigger;
   a roller, a sprayer and a sponge in the pocket configured to apply a disinfectant to the roller shade,
   wherein the disinfectant is supplied via a piping system to at least one of the roller, the sprayer or the sponge from a reservoir;
   an ultraviolet (UV) light source configured to provide UV light,
   wherein the UV light source is activated, increased in intensity and rotated closer to the roller shade, in response to other triggers,
   wherein the UV light source is configured to focus on a portion of the roller shade that was exposed outside of the pocket and into a room, and
   wherein the portion of the roller shade that was exposed outside of the pocket and into the room is based on a starting point set from when the roller shade is rolled up and based on an ending point from when the roller shade is extended over at least a portion of a window;
   the UV light source is held by interlocking fingers that interface with protrusions in a wall of the pocket for temporarily securing the UV light source to the wall of the pocket; and
   doors that interface with the pocket,
   wherein the doors are configured to close around an opening where the roller shade enters the pocket, in response to the UV light source being activated,
   wherein the doors when closed are configured to restrict the UV light from exiting the pocket, and
   wherein an inside surface of the doors when closed reflect the UV light back into the pocket.

2. The window shade pocket system of claim 1, wherein the UV light source at least partially sanitizes the roller shade, the pocket and components within the pocket.

3. The window shade pocket system of claim 1, further comprising a controller that controls a motor engaged to the roller shade, wherein the controller controls a speed of the motor to allow a portion of the roller shade to be under the UV light source for a predetermined amount of time to allow for sanitization of the portion of the roller shade.

4. The window shade pocket system of claim 1, further comprising an interlock configured to interface with the UV light source and temporarily restrict movement of the UV light source.

5. The window shade pocket system of claim 3, wherein the speed is based on at least one of an amount or extent of bacteria or viruses on at least one of the roller shade or in a room.

6. The window shade pocket system of claim 5, further comprising a central UV light source, wherein the roller shade provides a barrier from UV light from the central UV light source.

7. The window shade pocket system of claim 1, wherein the trigger that causes the roller shade to move faster or slower comprises at least one of applying of the disinfectant, an amount of time, a number of days, season of a year, higher sickness periods, input from motion sensors, input from locks, input from lighting systems, environmental conditions, lack of motion detected in an area, lights being turned off, a time of day being after business hours, a door lock being activated, or during a maintenance schedule.

8. The window shade pocket system of claim 1, wherein the reservoir sanitizes a chain that controls the roller shade, and wherein the UV light source is activated, in response to one of the other triggers that include at least one of pulling the chain or stopping the pulling of the chain.

9. The window shade pocket system of claim 1, wherein the roller shade is moved between the starting point and the ending point.

10. The window shade pocket system of claim 9, wherein the UV light source is at least one of within the pocket or in a compartment that interfaces with the pocket.

11. The window shade pocket system of claim 10, wherein the UV light source includes a plurality of UV light sources that selectively illuminate based on zone requirements.

12. The window shade pocket system of claim 11, wherein the plurality of UV light sources are coupled together and rotate together.

13. The window shade pocket system of claim 12, further comprises a lens over the UV light source, wherein the lens is configured to at least one of focus, broaden or diffuse the UV light from the UV light source onto at least a portion of the roller shade.

14. The window shade pocket system of claim 13, wherein the UV light source is in the form of strip lighting.

15. The window shade pocket system of claim 14, wherein the sponge is in the pocket, and wherein the sponge is configured to apply a disinfectant to the roller shade by sliding over the roller shade.

16. The window shade pocket system of claim 15, wherein the UV light source is at least one of removeable from a first bracket in the pocket or rotatable within the first bracket.

17. The window shade pocket system of claim 16, further comprising a sanitizing covering to at least one of protect or sanitize the roller shade.

18. The window shade pocket system of claim 1, further comprising a subsystem within the pocket for dispersing sanitizing solution.

* * * * *